United States Patent
Crank et al.

(10) Patent No.: US 9,918,820 B2
(45) Date of Patent: *Mar. 20, 2018

(54) IMPLANTABLE SLINGS AND ANCHOR SYSTEMS

(71) Applicant: Boston Scientific Scimed, Inc., Maple Grove, MN (US)

(72) Inventors: Justin M. Crank, Maple Grove, MN (US); Kathryn A. Bertelson, Buffalo, MN (US); Patricia M. Derus, Rogers, MN (US); Gary A. Rocheleau, Maple Grove, MN (US); Michael A. Knipfer, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/390,597

(22) Filed: Dec. 26, 2016

(65) Prior Publication Data

US 2017/0105828 A1    Apr. 20, 2017

Related U.S. Application Data

(63) Continuation of application No. 13/334,002, filed on Dec. 21, 2011, now Pat. No. 9,572,648.

(60) Provisional application No. 61/425,607, filed on Dec. 21, 2010, provisional application No. 61/425,639, filed on Dec. 21, 2010, provisional application No.
(Continued)

(51) Int. Cl.
| | | |
|---|---|---|
| *A61F 2/00* | (2006.01) | |
| *A61B 17/06* | (2006.01) | |
| *A61B 17/04* | (2006.01) | |
| *A61B 17/28* | (2006.01) | |
| *A61B 17/00* | (2006.01) | |

(52) U.S. Cl.
CPC ........ *A61F 2/0045* (2013.01); *A61B 17/0401* (2013.01); *A61B 17/0483* (2013.01); *A61B 17/06109* (2013.01); *A61B 17/2812* (2013.01); *A61B 2017/00867* (2013.01); *A61B 2017/0417* (2013.01); *A61B 2017/0427* (2013.01); *A61B 2017/0437* (2013.01); *A61B 2017/0461* (2013.01)

(58) Field of Classification Search
CPC .................. A61F 2/0045; A61F 2/0063; A61F 2250/0031; A61F 2250/0051; A61F 2/82; A61F 2002/4495; A61F 2/441; A61F 2250/0012; A61F 2250/0048; A61F 2/02; A61F 2/04; A61F 2/0036; A61B 2017/00805
See application file for complete search history.

(56) References Cited

U.S. PATENT DOCUMENTS 9,572,648 B2 * 2/2017 Crank .................... A61F 2/0045
2012/0157761 A1 * 6/2012 Crank ................. A61B 17/0401
                                                                      600/37

FOREIGN PATENT DOCUMENTS

WO    WO 2007149348 A2 * 12/2007 ......... A61B 17/0401

* cited by examiner

*Primary Examiner* — Christine H Matthews
(74) *Attorney, Agent, or Firm* — Brake Hughes Bellermann LLP

(57) ABSTRACT

Various embodiments of a mesh or implant systems are provided. The implants can include one or more anchors, arms and the like. The anchors can include hingeable or patterned finger extension to facilitate tissue penetration and retention. Various tensioning and adjustment mechanisms, devices and methods are further provided for the implant systems.

18 Claims, 11 Drawing Sheets

Related U.S. Application Data

61/426,075, filed on Dec. 22, 2010, provisional application No. 61/426,086, filed on Dec. 22, 2010.

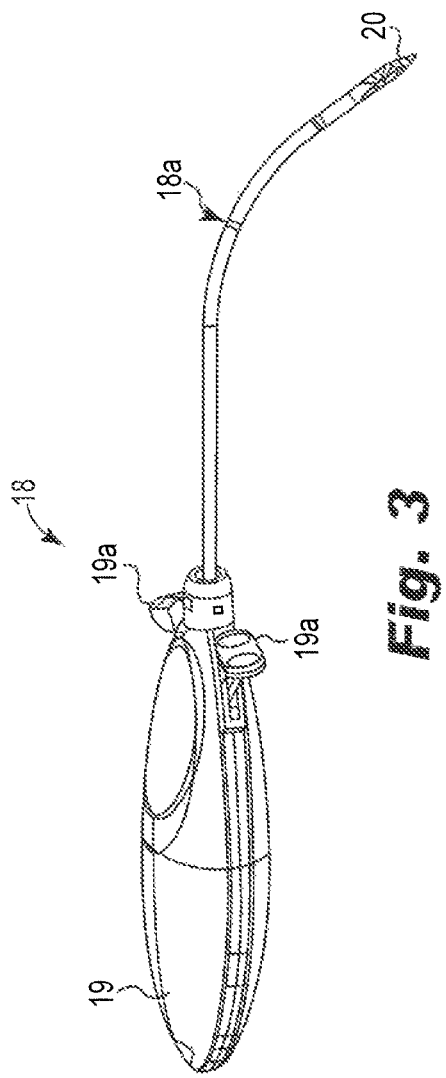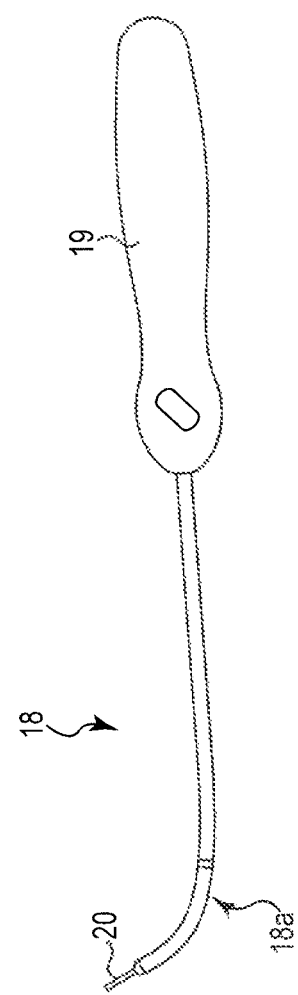

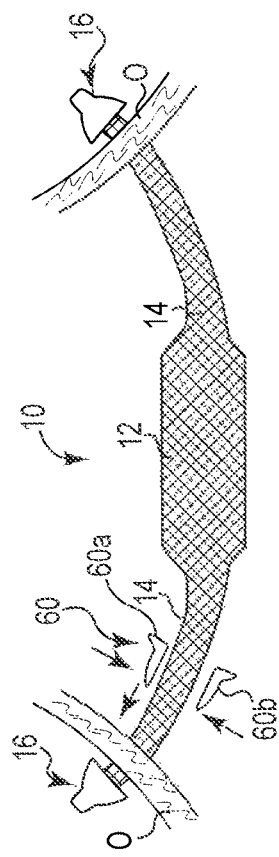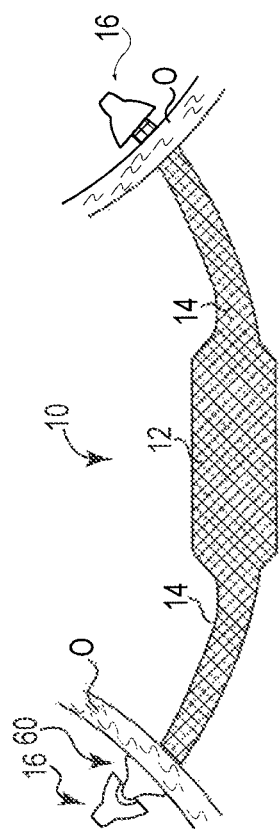

IMPLANTABLE SLINGS AND ANCHOR SYSTEMS

PRIORITY

This Application is a continuation of U.S. Nonprovisional patent application Ser. No. 13/334,002, filed Dec. 21, 2011, which claims priority to and the benefit of U.S. Provisional Patent Application No. 61/425,607, filed Dec. 21, 2010, U.S. Provisional Patent Application No. 61/426,075, filed Dec. 22, 2010, U.S. Provisional Patent Application No. 61/426,086, filed Dec. 22, 2010, and U.S. Provisional Patent Application No. 61/425,639, filed Dec. 21, 2010; Each of the above-identified applications and disclosures are incorporated fully herein by reference.

FIELD OF THE INVENTION

The present invention relates generally to surgical methods and apparatus and, more specifically, to surgically implantable mesh, sling or anchoring devices for use in treating incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic implant systems as well as anchoring devices and methods used in treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the anchoring devices can be provided with implants or slings (e.g., mesh slings) adapted to support tissue, wherein the anchoring devices are fixated to target tissue. The target tissue for anchoring can include endopelvic fascia, muscles, ligaments, and the like. Certain embodiments are directed to anchoring in the obturator tissue.

Various embodiments of the sling or implant system can include anchor members or devices including extending members adapted to facilitate fixation with the target tissue. The extending members of the anchor devices can be hingeable or pivotable relative to a portion of the anchor device, such as the body portion.

Other embodiments of the anchor device can include extending or extendable finger extensions. The finger extensions can be sized and patterned to provide various tissue penetration or retention characteristics for the anchors. The anchors can be cut or formed from a metallic material, e.g., Nitinol, such that uniquely patterned anchors can be constructed very small, yet strong and durable. In various embodiments, the anchor construct can be formed or cut from Nitinol into an initial shape or pattern. The finger extensions can be splayed or otherwise expanded and then heated to a desired or threshold temperature (e.g., 1000 degrees Fahrenheit) to heat set the expanded finger configuration for use.

Embodiments of the implant can include a tensioning feature in the form of a sliding spacer element. The spacer element can be adapted to engage and slide along a portion of the sling, e.g., the extension portion, through tissue for positioning between the fixated anchor and the target tissue. The spacer element can include tines or other anchor-like portions adapted to penetrate and engage tissue during the adjustment procedure. Other embodiments of the implant can include one or more extending sutures spanning between the support portion and the respective anchor to facilitate tensioning adjustment.

Embodiments of the present invention may be incorporated into or provided with various commercial products marketed by American Medical Systems of Minnetonka, Minn., as the MiniArc® Single-Incision Sling, Elevate® implants, and like implant and anchoring systems used to treat various pelvic disorders, e.g., incontinence, prolapse, etc.

BRIEF DESCRIPTION OF THE DRAWINGS

FIGS. 3-4 show introducer needle devices in accordance with embodiments of the present invention.

FIGS. 25-26 show an elongate sling implant and a spacer tensioning feature in accordance with embodiments of the present invention.

DETAILED DESCRIPTION OF PREFERRED EMBODIMENTS

Figure 1:
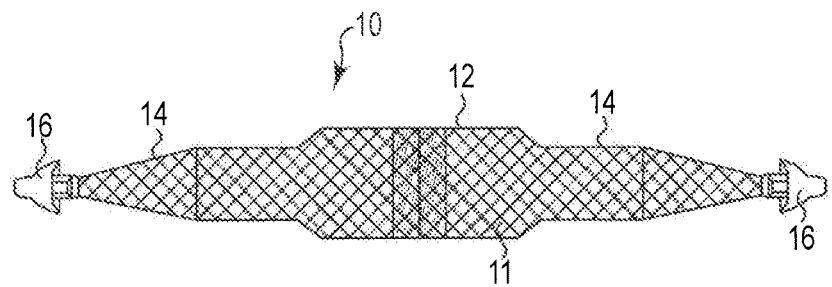
FIGS. 1-2 show implant and anchoring devices in accordance with embodiments of the present invention.
Figure 2:
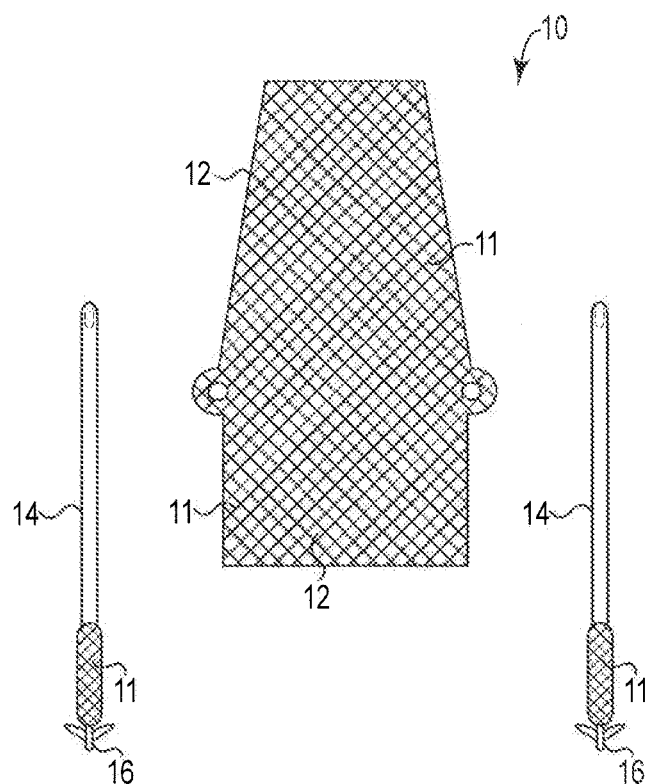

Referring generally to FIGS. 1-2, various embodiments of implantable sling or mesh systems 10 and methods adapted to include certain anchoring and other implant structures or devices are disclosed herein. In general, the implant systems 10 can include a support portion 12, and extension or arm portions 14 having anchors 16 provided therewith. Various anchor 16 embodiments provided herein can include one or more extending tines or barbs to promote tissue fixation. FIGS. 1-2 show implant systems 10 having conventional anchors 16. Various portions of the implant systems 10 can be constructed of polymer materials from a mesh of filaments 11. Certain embodiments can be constructed of or from a film or sheet material of polypropylene, polyethylene, fluoropolymers or like compatible materials.

The various implants or systems, features devices, and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2011/0144417, 2010/0105979, 2002/151762 and 2002/147382. Accordingly, the above-identified disclosures are fully incorporated herein by reference in their entirety.

Embodiments of the slings or implants 10 of the present invention can be introduced and deployed within the patient using one or more introducer needle devices. As shown in FIGS. 3-4, the needle device 18 can include a handle portion 19 and a needle length 18a that can be non-linear or curved in certain embodiments to facilitate deployment and navigation through tissue and around anatomical structure. In other embodiments, the needle devices 18 can be generally straight, helical, or take on a myriad of other shapes and designs to facilitate deployment and use. A distal tip or portion 20 of the needle device 20 can receive or engage with the anchors 16 of the present invention to facilitate deployment and tissue fixation. The handle 19 can include one or more actuators 19a (e.g., slider, button, etc.) operably connected to the needle length 18a to selectively move (retract or extend) a distal portion 20 of the needle length 18a, as shown in FIG. 3. In such embodiments, the anchor 16 can be securely engageable with the distal tip 20 such that activation of the one or more actuators 19a selectively disengages the anchor 16.

Referring generally to FIGS. 5-15, various embodiments of sling or implant anchoring devices 16 are shown. Such anchoring features facilitate positioning and engagement of the anchor 16 in target tissue, such as the obturator internus or like muscle or tissue.

In certain embodiments, the anchors 16 of the present invention 10 can include laterally expandable fingers or arm portions 30. The fingers 30 are adapted to expand at deployment to capture tissue and resist pullout. The expandable fingers 30 configuration allows the anchors 16 to be sized relatively small while still providing large pullout strengths. The anchors, or portions thereof, can be constructed of compatible polymer or metal materials. In certain embodiments the anchors 16 can be constructed, in whole or in part, of polypropylene or a like polymer material. Other embodiments of the anchors 16 can be constructed, in whole or in part, of Nitinol or a like metal material.

Figure 7:
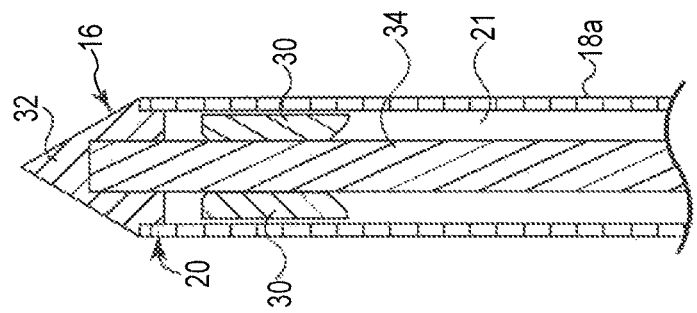
FIGS. 5-15 show hingeable anchor devices with extending finger or arm portions in accordance with embodiments of the present invention.

The anchors 16 can include a head portion 32, the one or more expandable fingers or arms 30, and a shaft portion 34. The shaft 34 can be configured as a wire, cable or mesh material (e.g., flat, braided, etc.) for integrating or otherwise providing with the mesh implant 10 or implant support portion 12. The shaft 22 can also include a lumen or like engagement feature or channel to permit engagement with a needle or other device. In various embodiments, during deployment, the anchors 16 can be retained within an inner lumen or cannula 21 of the needle device 18 (e.g., needle 18a). A portion, such as the head portion 32, can extend a distance out from the end of the needle lumen 21 to facilitate tissue penetration and navigation during deployment, as depicted in FIG. 7. In general, however, the fingers 30 will remain retracted within the lumen 21 until tissue fixation is desired. Then the anchor 16 can be further extended out of the lumen 21 until the fingers 30 are no longer being contained by the inner walls of the lumen 21, such that they will automatically spring or laterally extend, or they will extend through manual actuation. Various biased portions or hinges can be included to facilitate this automatic extension, including the use of springs or materials having shape-memory characteristics (e.g., polymer or metal).

Figure 6:
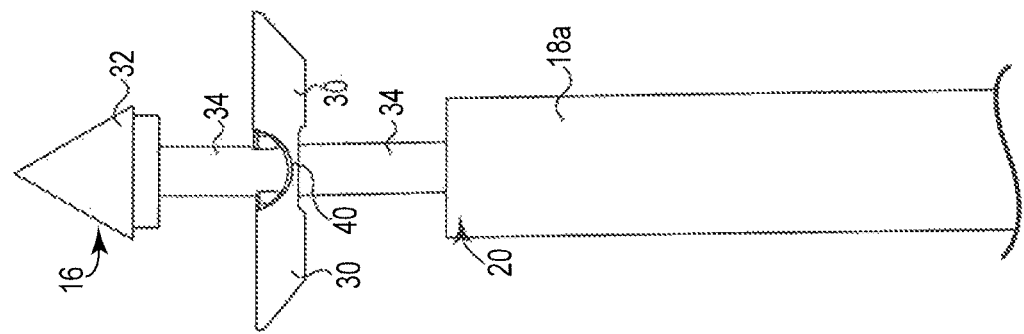
Figure 5:
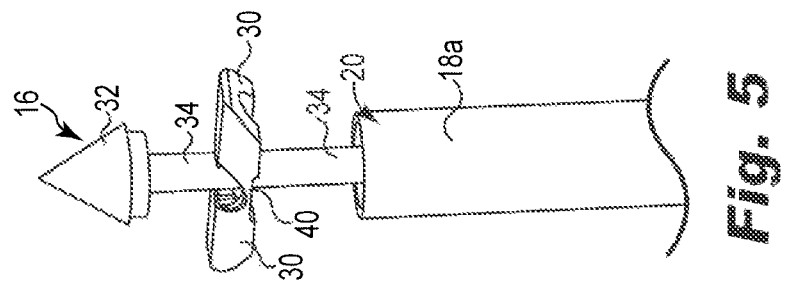

FIGS. 5-7 show embodiments of the anchor device 16 having opposing and selectively extendable fingers 30. Again, the anchor 16 device and corresponding fingers 30 are adapted to seat at least partially within the lumen 21 of the needle device 18. Such embodiments can include a narrow bridging portion 40 adapted to function as a living hinge. The bridging portion 40 can bias the fingers 30 into the extended (lateral) position relative to the shaft 34 when ejected or otherwise extended out of the lumen 21. A spring or like biasing member can also be included in operable communication with the fingers 30 to bias them outward or laterally upon release from the constraints of the lumen 21. In certain embodiments, the bridging portion 40 is constructed of a polymer material, such as polypropylene, along with the rest of the anchor 16. Various materials and material combinations can be used to construct all or part of the anchor 16.

Figure 8:
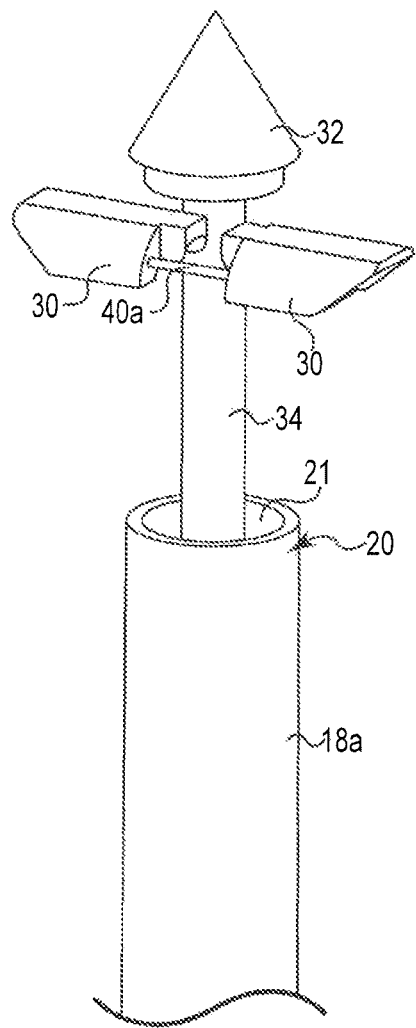
Figure 9:
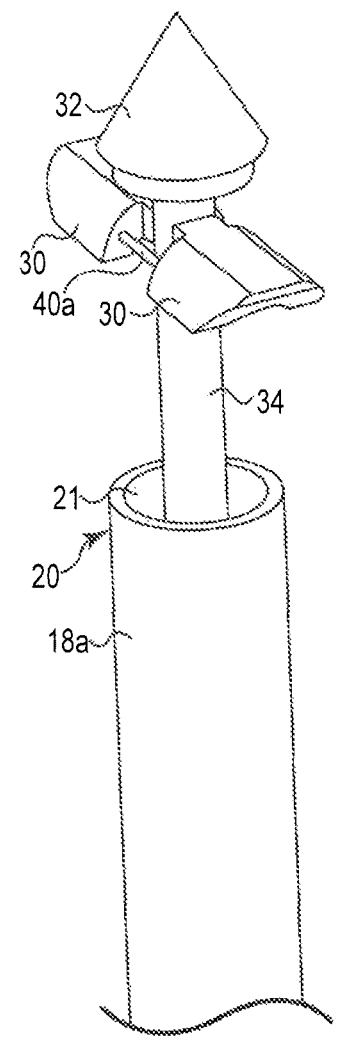

As shown in FIGS. 8-9, the bridging portion 40 can include a thin metal wire or member 40a, such as Nitinol, to provide the hinging action for the fingers 30. Again, the hinging can occur automatically when the anchor 16 and fingers 30 are released from the constraints of the lumen 21, or through manual actuation. For instance, pulling or like actuation of the shaft portion 34 can facilitate the selective expansion of the fingers 30.

Figure 11:
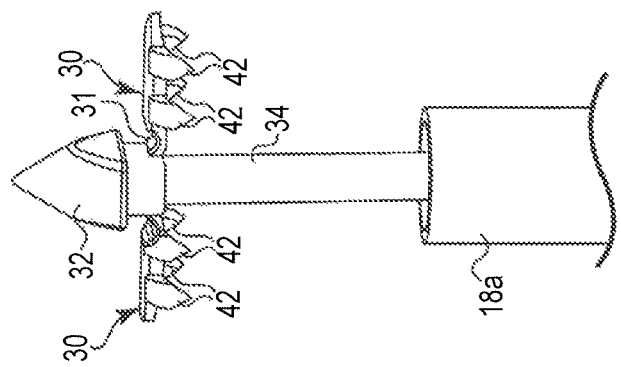
Figure 10:
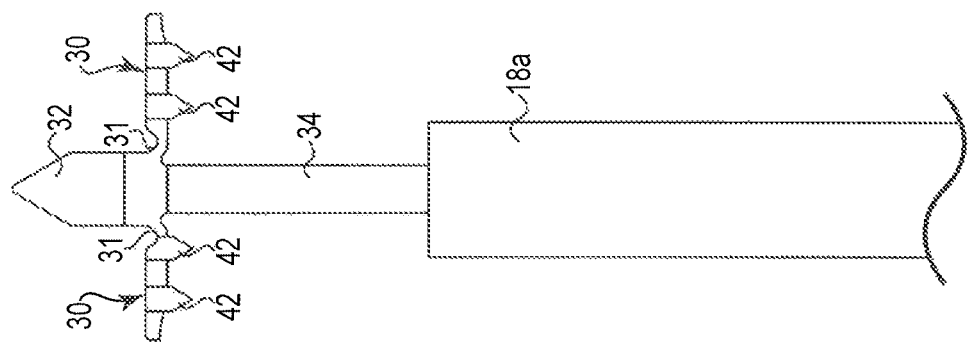

Other embodiments of the anchors 16 are shown in FIGS. 10-11, wherein the fingers 30 include one or more extending teeth-like or tissue grasping elements 42. Upon lateral expansion of the fingers 30 about hinge portions 31, the grasping elements 42 can further facilitate tissue fixation to improve anchoring stability and to resist pullout.

Figure 12:
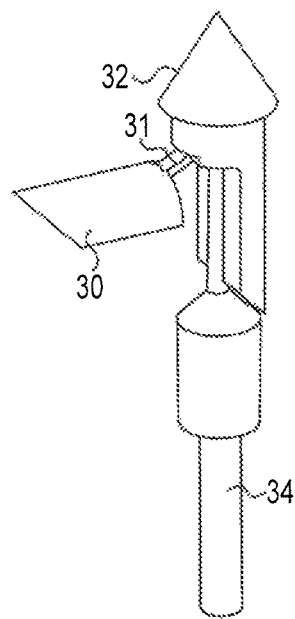
Figure 13:
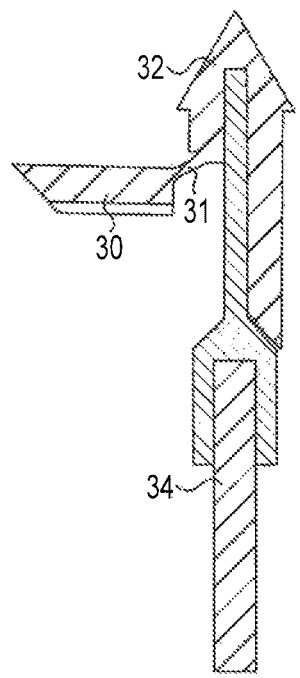

Embodiments of the anchors 16, as shown in FIGS. 12-13, can include a single hinging or laterally extendable finger 30. Again, the fingers 30 can hinge about hinging portion 31.

Figure 14:
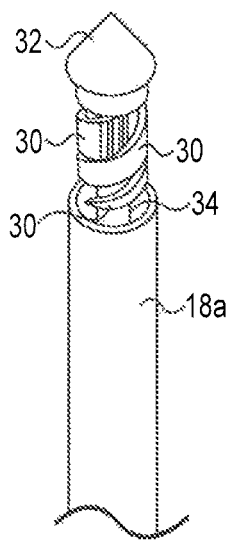
Figure 15:
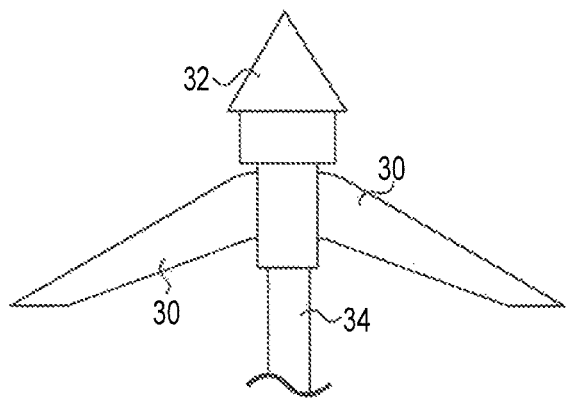
Figure 16:
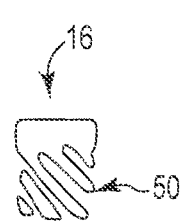
FIGS. 16-24 show anchor devices having extending shape-memory finger or arm portions in accordance with embodiments of the present invention.
Figure 17:
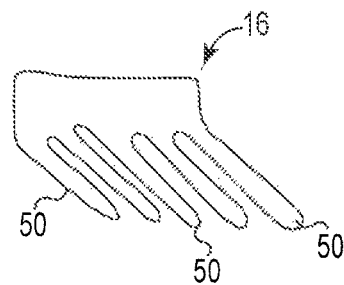

FIGS. 14-15 depict an embodiment of the anchor device 16 having one or more fingers 30 configured such that they are twisted or wrapped around a portion of the shaft 34 during deployment or retention within the lumen 21. To facilitate twisting the fingers 30 around the shaft 34 (FIG. 14), the fingers 30 must be sufficiently flexible. It should be noted that the fingers 30 of other embodiments can have similar flexibility to facilitate manipulation of the anchors 16 and increased tissue fixation and pullout resistance. When the fingers 30 of this embodiment clear the restriction of the lumen 21 during ejection or deployment of the anchor device 16 from the needle 18, the fingers 30 will spring out to their respective extension configurations, as shown in FIG. 15.

Figure 18:
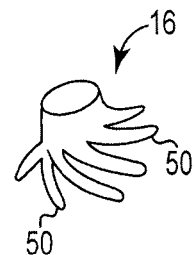
Figure 19:
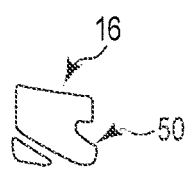
Figure 20:
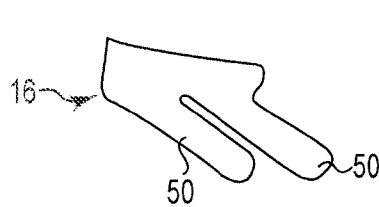
Figure 21:
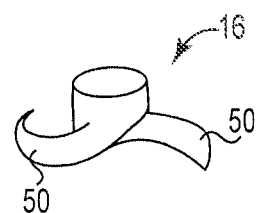
Figure 22:
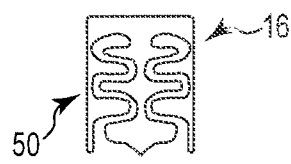
Figure 23:
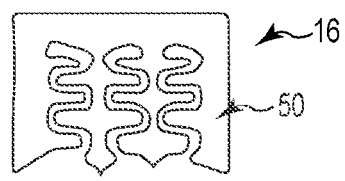
Figure 24:
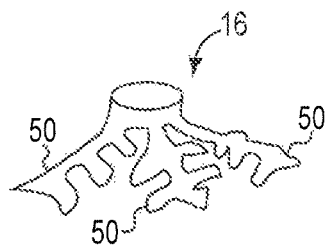

FIGS. 16-24 show various anchor devices 16 having exemplary finger features 50, wherein the anchors 16, or at least a portion thereof, are constructed of a metal material, such as Nitinol. These fingers 50 can be cut, formed or otherwise provided (e.g., laser cut, stamped, etched, etc.) with the anchors 16 in an initial configuration (FIGS. 16, 19, 22-23). Then, the fingers 50 can be splayed out to a desired configuration where the fingers 50 can provide desired tissue fixation properties to resist pullout forces. Once the fingers 50 are splayed out in the desired pattern and configuration, the portion of the anchor 16 having the fingers 50, or the entire anchor 16, can be heated by known means to a temperature of approximately 1000 degrees Fahrenheit to set the finger 50 layout and configuration in place (FIGS. 18, 21, and 24). Other known heating means and methods, and temperature settings, for manipulating and setting Nitinol and like materials in this manner can be employed with such embodiments of the present invention. The various options for the shapes and sizes of the fingers 50 is nearly endless, thereby providing a shape-memory anchor 16 having desirable fanned-out fingers 50 in the final configuration of the anchors 16 to promote tissue penetration and anchor retention. The anchors 16 and corresponding finger 50 features can be integrated or provided with, directly or indirectly, compatible mesh or like implant devices 10 for treating various pelvic disorders.

Referring generally to FIGS. 25-26, an embodiment of the mesh or sling implant 10 is provided with at least one tensioning feature. The implant 10 can generally comprise the above-disclosed implant 10 of elongate mesh having extension portions 14, a support portion 12 and distal tined anchors 16. As shown in FIG. 25, the implant 10 can be positioned to support the urethra or bladder neck with the support portion 12, with the extension portions spanning to the obturator internus muscle O. In addition, the implant 10 can include the tensioning feature in the form of a sliding spacer element 60. The spacer element 60 can be adapted to engage and slide along a portion of the sling, e.g., extension portion 14 (FIG. 25). The spacer element 60 can include tines or other anchor-like portions adapted to penetrate and engage tissue during the adjustment procedure.

In certain embodiments, the spacer element 60 is a two-piece construct having a first portion 60a and a second portion 60b adapted to snap together, capturing a portion of the extension portion 14 in a channel or like opening or portion in the element 60. The snapping engagement of the portions 69a, 60b can be facilitated by mating post and apertures, a clip, press-fit members or features, snap-fit surfaces, locking detents, and the like. Once snapped in place, the element 60 can be slid up or down the extension portion generally free of obstructions. To adjust tension in the sling 10, e.g., increase support pressure of the support portion 12 on the urethra or bladder neck, the spacer element 60 can be slid up or out along the extension portion 14, through the obturator internus muscle (or other tissue having an anchor 16 fixed therein), and up into abuttable contact with the anchor 16 on the other side of, or within, the target anchoring tissue, as shown in FIG. 26. Various embodiments of the spacer element 60 can be sized and shaped to engage the anchor 16, thereby securing it in place between the anchor 16 and the tissue. In one embodiment, the tip or distal end portion of the spacer element (shaped and configured like an anchor 16) can be seated into an aperture or channel at the proximal end of the anchor 16, at least to some measurable depth. While the anchor-like spacer element 60 is shown on a single side of the implant, one or more elements 60 can be used and introduced on either or both sides of the implant 10 and respective extension portions 14. Further, spacer elements 60 can be provided for use as a tensioning feature in various sizes and shapes, thereby providing different spacing and tensioning results for the implant 10. In addition, the elements 60 can be constructed in a one-piece, two-piece or like configuration. A needle device can be included to engage and position the element 60 to facilitate sliding movement, tissue engagement and the appropriate tensioning. Multiple elements 60 can be employed with any particular surgical application.

Figure 27:
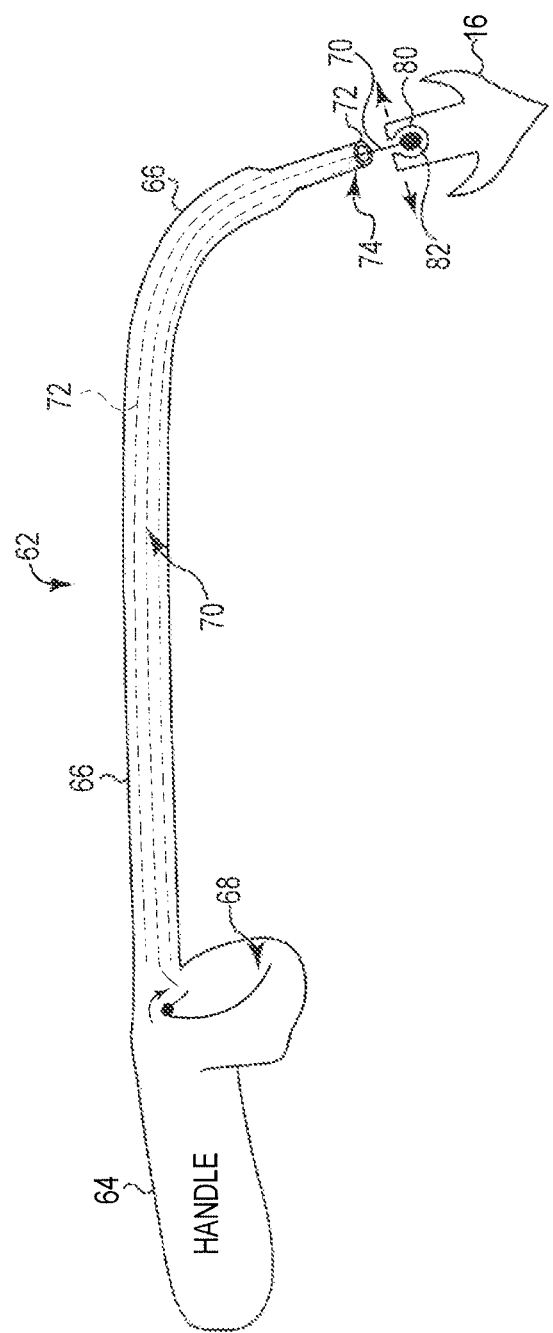
FIG. 27 shows an introducer needle device having a bulbous portion extending from an actuatable wire for selective engagement with an anchor in accordance with embodiments of the present invention.

In addition to those needle devices 18 disclosed and incorporated herein, a needle device 62 in accordance with the embodiment of FIG. 27 can be used as well. This needle device 62 can be used to advance the anchors 16 of the various implant 10 embodiments disclosed herein, as well as the element 60. The needle device 62 can include a handle 64, a needle 66, and a trigger 68 or like actuation mechanism. The trigger 68 can include a button, slider, or like mechanism or device, and is in operable communication with a wire 70 or similar member extending through the internal lumen 72 of the needle 66. As such, actuation of the trigger 68 can selectively retract or extend the wire 70 from the distal end 74 of the needle lumen 72. The wire 70 distal end can include a bulbous or other shaped element 82.

In certain embodiments, the anchors 16 can include a lumen or recess 80 adapted to engage with the bulbous element 82 at a distal end of the wire 70. The configuration of the recess 80 is adapted to permit deformable or distortable engagement with the bulbous element 82. For example, a polymer constructed recess 80 area in the anchor 16 can provide a level of deformation to allow force fitting of the bulbous element 29 into and out of the anchor 16. As the bulbous element 82 is pulled out of the recess 80 using a pulling force, the walls of the anchor 16 around the recess 80 can expand or flex out enough to permit the bulbous element 82 to unseat and eject from the recess 80. Using the device 62 to push the anchor 16 into tissue will retain the bulbous element 82 within the recess 80 of the anchor 16. Once the anchor 16 is fixated or engaged with the target tissue, the wire 70 can be withdrawn via actuation back into the needle, thereby applying the requisite pulling force to eject the bulbous element 82 from the recess 80. Again, actuation of the mechanism 68 can facilitate this selective engagement between the components.

Figure 28:
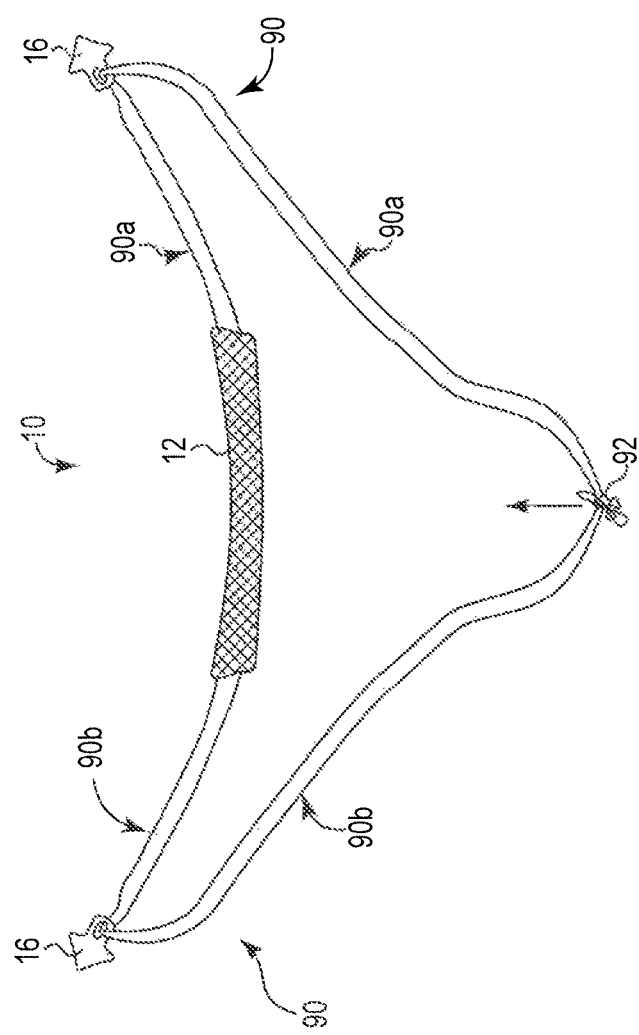
FIG. 28 shows an elongate sling implant having spanning sutures to facilitate tensioning and adjustment in accordance with embodiments of the present invention.

Various embodiments of the mesh or sling implant 10 are shown with one or more sutures 90 or like flexible or filament members spanning between the support portion 12 and the corresponding anchors 16, as shown in FIG. 28. Such embodiments are adapted to provide bilateral adjustability of the sling 10. Each side of the implant 10 can include a distinct suture such that one side has a suture 90a and the other side has a suture 90b. The adjustment enables sling positioning and tensioning independently for each side of the sling (e.g., between support portion 12 and the respective anchor 16). The sutures 90 are configured to easily slide through the anchor 16 (e.g., aperture) and the mesh support portion 12 (e.g., around mesh filaments or via an eyelet in the support portion 12). Ends of the sutures 90a, 90b can be fastened to one another via a feature 92 such as a sliding knot, a staple, a clip, a grommet, a ring, or like element. The feature 92 can be slid upward toward the sling support portion 12. In certain embodiments, portions of the anchors 16 can include mesh or like porous material to promote tissue in-growth. The sutures 90a, 90b can be resorbable in certain embodiments.

Figure 29:
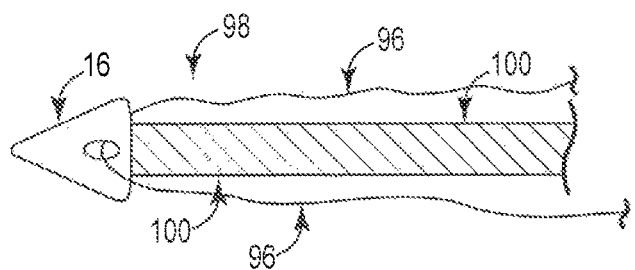
FIGS. 29-32 show introducer and like implant deployment devices in accordance with embodiments of the present invention.
Figure 30:
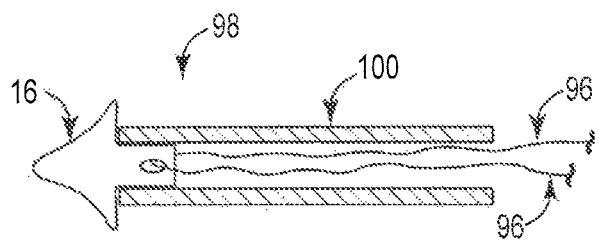

Referring generally to FIGS. 29-32, various embodiments can include an introducer device adapted for use with implant systems 10 having one or more sutures 96 (or other sutures or flexible members as disclosed herein). In one embodiment, as shown in FIGS. 29-30, an introducer device 98 includes a needle portion 100 adapted to hold or receive and pass the sutures 96 via a connector. The passage of the device 98 and connected suture 96 can be partially or completely along a respective tissue path. The sutures 96 can pass with the device 98 outside of the needle 100 (FIG. 29) or within a lumen of the needle 100 (FIG. 30).

Figure 31:
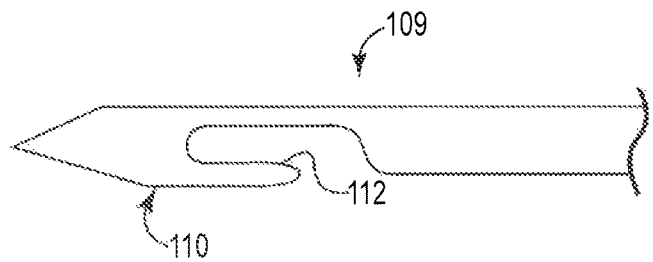
Figure 32:
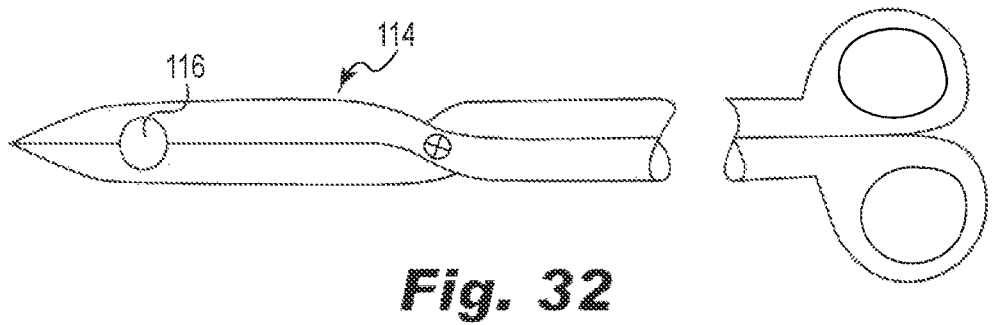

Embodiments of the system 10 can include an introducer device 109 having a catch portion 110 defining at least one slot or groove 112, as shown in FIG. 31. The slot 112 can be used to engage, grab and pull respective sutures therein for deployment or adjustment during introduction and tensioning of the implant 10. Other embodiments of an introducer device 114 can be constructed similar to scissors or other cutting devices, as shown in FIG. 32. The scissor-like device 114 can define an aperture or opening 116 therein to permit receipt of a suture or like element, such as a suture loop, mesh filament, and the like. To engage the suture, the device 114 can be pivoted open to permit engagement with the suture within the opening 116. The end of the device 114 can then be closed to trap the suture in the opening 116 for guidance during the procedure, and eventual release upon completion of the deployment, adjustment or implantation process. Other introducer and deployment devices known to those skilled in the art can be utilized as well without deviating from the scope of the present invention.

The implant systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant system for treating pelvic disorders, comprising:
    an implant having a support portion, at least one extension portion and at least one anchor device disposed at an end portion of the at least one extension portion, the at least one anchor device having a tapered tip portion and one or more extending barbs and adapted to extend through target tissue; and
    a spacer element including a tapered tip portion and one or more extending barbs extending out generally radially from opposing sides of a longitudinal axis of the spacer element, the spacer element including a first portion and a second portion, the second portion being coupled to the first portion, the spacer element adapted to slidably engage the at least one extension portion such that the spacer element is slidable along the at least one extension portion and through the target tissue for positioning between the at least one anchor device and the target tissue to provide tensioning adjustment for the elongate implant.

2. The system of claim 1, wherein the at least one extension portion includes two extension portions.

3. The system of claim 2, wherein the at least one anchor device includes two extending barbs.

4. The system of claim 1, wherein the at least one anchor device includes two extending barbs.

5. The system of claim 1, wherein the at least one anchor device is generally arrow-shaped.

6. The system of claim 1, further including a second spacer element.

7. The system of claim 1, wherein at least the support portion of the implant is constructed of a mesh material.

8. The system of claim 1, wherein the implant is constructed of a mesh material.

9. The system of claim 1, wherein the target tissue is the obturator internus muscle.

10. The system of claim 1, wherein the first portion and the second portion are operably attachable around the at least one extension portion.

11. An implant system for treating pelvic disorders, comprising:
    an implant having a support portion, first and second extension portions, a first anchor provided at an end portion of the first extension portion, and a second anchor provided at an end portion of the second extension portion, the first and second anchors including a tapered distal portion and one or more extending barbs and adapted to extend through target tissue; and
    a spacer element having a tapered distal portion and one or more transversely extending barbs, the spacer element including a first portion and a second portion, the second portion being coupled to the first portion, the spacer element adapted to surround a portion of at least the first extension portion such that the spacer element is slidable along the first extension portion and through the target tissue for positioning between the first anchor and the target tissue to provide tensioning adjustment for the implant.

12. The system of claim 11, wherein the first and second anchors include two extending barbs.

13. The system of claim 11, wherein at least one of the first and second anchors is generally arrow-shaped.

14. The system of claim 11, further including a second spacer element.

15. The system of claim 11, wherein at least the support portion of the implant is constructed of a mesh material.

16. The system of claim 11, wherein the implant is constructed of a mesh material.

17. The system of claim 11, wherein the target tissue is the obturator internus muscle.

18. The system of claim 11, wherein the first portion and the second portion are operably attachable around the first extension portion.

\* \* \* \* \*